United States Patent
Coy et al.

(10) Patent No.: US 6,465,613 B1
(45) Date of Patent: Oct. 15, 2002

(54) HYDROPHILIC SOMATOSTATIN ANALOGS

(75) Inventors: David H. Coy, New Orleans, LA (US); William A. Murphy, Slidell, LA (US); Eugene A. Woltering, Kenner, LA (US); Joseph A. Fuselier, New Orleans, LA (US); George Drouant, Mandeville, LA (US)

(73) Assignee: Tulane University, New Orleans, LA (US)

( * ) Notice: Subject to any disclaimer, the term of this patent is extended or adjusted under 35 U.S.C. 154(b) by 0 days.

(21) Appl. No.: 09/196,259

(22) Filed: Nov. 19, 1998

(51) Int. Cl.$^7$ ............................................... A61K 38/16
(52) U.S. Cl. ..................... 530/311; 530/300; 530/327; 530/329; 514/5; 514/14; 514/15; 424/1.11; 424/1.69
(58) Field of Search ................................. 530/311, 300, 530/329, 327; 424/1.11, 1.69; 514/14, 15, 5

(56) References Cited

U.S. PATENT DOCUMENTS

| | | |
|---|---|---|
| 4,904,642 A | 2/1990 | Coy et al. |
| 5,073,541 A | 12/1991 | Taylor et al. |
| 5,411,943 A | 5/1995 | Bogden |
| 5,597,894 A | 1/1997 | Coy et al. |
| 5,620,675 A | 4/1997 | McBride et al. |
| 5,633,263 A | 5/1997 | Coy et al. |
| 5,708,135 A | 1/1998 | Coy et al. |
| 5,750,499 A | 5/1998 | Hoeger et al. |
| 5,753,627 A | 5/1998 | Albert et al. |
| 5,770,687 A | 6/1998 | Hornik et al. |
| 6,017,512 A | 1/2000 | Dean et al. ................. 424/1.69 |

FOREIGN PATENT DOCUMENTS

| | | |
|---|---|---|
| WO | WO 91/01144 | 2/1991 |

OTHER PUBLICATIONS

Bakker et al., "Iodine 131 labelled octreotide: not an option for somatostatin receptor therapy" *Eur. J. Nucl. Med.* 23:775–81 (1996).

Breeman et al., "Studies on radiolabeled somatostatin analogues in rats and in patients" *Q. J. Nucl. Med.* 40:209–20 (1996).

Kawai et al., "Monoiodo–D–tyrosine, an artificial amino acid radiopharmaceutical for selective measurement of membrane amino acid transport in the pancreas" *Nucl. Med. Biol.* 17:369–376 (1990).

Meyers et al., "Multiply Radioiodinated Somatostatin Analogs Induce Receptor–Specific Cytotoxicity," *J. of Surgical Research* 76:154–158 (1998).

Shimon et al., "Somatostatin Receptor Subtype Specificity in Human Fetal Pituitary Cultures. Differential Role of SSTR2 and SSTR5 for Growth Hormone, Thyroid–stimulating Hormone, and Prolactin Regulation," *J. Clin. Invest.* 99:789–798 (1997).

Lawrence et al., "Radiosensitization of pancreatic cancer cells by 2'–2'–difluoro–2'–deoxycytidine" *Int. J. Radiat. Oncol. Biol. Phys.* 34:867–872 (1996).

Pandey et al., "Shedding some light on tumours" *Chemistry & Industry* 739–743 (1998).

*Primary Examiner*—Michael Borin
(74) *Attorney, Agent, or Firm*—Clark & Elbing LLP

(57) ABSTRACT

The invention features novel somatostatin analogs that may be readily labeled with toxic or non-toxic detectable labels. These unlabeled and labeled analogs are useful for specifically targeting somatostatin receptor bearing cells, in particular neoplastic cells. Labeled analogs are useful, for example, for tumor localization and detection. Where labeled with a toxic label (e.g., radioactivity), the analogs are useful for the targeted delivery of toxicity to somatostatin receptor-bearing cells, in particular neoplastic cells.

Also disclosed are methods for treating and detecting neoplasms, and methods for imaging somatostatin receptor-bearing cells.

20 Claims, No Drawings

HYDROPHILIC SOMATOSTATIN ANALOGS

BACKGROUND OF THE INVENTION

The invention relates to somatostatin analogs which find use, e.g., in the detection, imaging, or specific targeting of somatostatin receptor-expressing cells, particularly neoplastic cells.

Somatostatin (SRIF) is an endogenous neuropeptide that acts as a regulator of growth hormone (GH) secretion. Somatostatin additionally inhibits the release of other pituitary hormones (i.e., thyrotropin, prolactin) and suppresses both exocrine and endocrine functions of the gastro-enteropancreatic system. Native human SRIF has the following amino acid sequence (from the amino to carboxy termini): Ala-Gly-c[Cys-Lys-Asn-Phe-Phe-Trp-Lys-Thr-Phe-Thr-Ser-Cys]

At least five types of somatostatin receptors are known to exist and are expressed on cells in the brain and in peripheral tissues. In addition, somatostatin receptors are present on certain types of tumors, including carcinoids, islet cell tumors, small cell lung tumors, CNS (neuroendocrine) tumors and some thyroid carcinomas. At least some of the biological effects of somatostatin have been associated with the binding of somatostatin to a particular type of receptor (e.g., binding to somatostatin receptor type 5 results in a different biological response than does the binding to somatostatin receptor type 2).

SUMMARY OF THE INVENTION

In general, the invention features novel somatostatin analogs which may be readily detectably labeled, e.g., with a radioactive label. Such analogs are useful for intraoperative tumor localization, and for imaging somatostatin receptor-bearing cells and specifically targeting toxicity (e.g., radioactivity) to such cells.

According, in a first aspect, the invention features a somatostatin analog of the formula: W-X-(A-B)$_n$-somatostatin peptide where A is D-tyrosine, L-tyrosine, D-3-iodotyrosine, L-3-iodotyrosine, D-3,5-diiodotyrosine, L-3,5-diiodotyrosine, D-4-aminophenylalanine, or L-4-aminophenylalanine; B is D-lysine, L-lysine, D-arginine, L-arginine, D- or L-1,3-diaminopropionic acid, D- or L-1,4-diaminobutanoic acid, D-NH$_2$—CH(Z)—CO$_2$H, or L-NH$_2$—CH(Z)—CO$_2$H, wherein Z is (CH$_2$)$_y$NH$_2$, wherein y is 1–10; X is A or B; W is absent or is NH$_2$(CH$_2$)$_t$CO, wherein t=2–10; n is 1–10; and each (A-B) may be the same as or different from each other (A-B). In one preferred embodiment, the analog is attached to a detectable label. The detectable label may be toxic (e.g., radioactive) or non-toxic.

In another embodiment of the first aspect of the invention, the analog is indirectly attached to the detectable label. For example, the analog may be attached to a chelating group that is attached to the detectable label.

In another embodiment of the first aspect of the invention, the analog is directly attached to the detectable label.

In another embodiment of the first aspect, the detectable label is an iodine label that is attached to a tyrosine residue or a phenylalanine residue of the analog. The iodine label may be radioactive (e.g., a short-acting radioactive iodine label, such as [123]I (t½=hours) or [131]I (t½=days)). Preferably, the analog includes a tyrosine residue, and the iodotyrosine residue of the analog does not undergo enzymatic deiodination. More preferably, the tyrosine residues is a D-tyrosine residue, and the D-iodotyrosine residue does not undergo enzymatic deiodination.

In other embodiments of the first aspect, the analog has a biological activity that is greater than or equal to the biological activity of the somatostatin peptide of the analog; the analog is used as an anti-neoplastic therapeutic; the analog is in a pharmaceutically acceptable carrier; the analog is used to specifically target an angiogenic blood vessel or a cell thereof; the analog is used for imaging a cell expressing a receptor to which the analog specifically binds; and the analog is used to detect a cell expressing a receptor to which the analog specifically binds (e.g., the analog is used for intraoperative tumor localization).

In a second aspect, the invention features a method for treating or alleviating a neoplasm in an animal that includes the steps of: (a) providing an animal including a somatostatin receptor-bearing neoplastic cell; (b) providing a somatostatin analog having the formula:

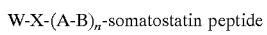
W-X-(A-B)$_n$-somatostatin peptide where A is D-tyrosine, L-tyrosine, D-3-iodotyrosine, L-3-iodotyrosine, D-3,5-diiodotyrosine, L-3,5-diiodotyrosine, D-4-aminophenylalanine, or L-4-aminophenylalanine; B is D-lysine, L-lysine, D-arginine, L-arginine, D- or L-1,3-diaminopropionic acid, D- or L-1,4-diaminobutanoic acid, D-NH$_2$—CH(Z)—CO$_2$H, or L-NH$_2$—CH(Z)—CO$_2$H, wherein Z is (CH$_2$)$_y$NH$_2$, wherein y is 1–10; X is A or B; W is absent or is NH$_2$(CH$_2$)$_t$CO, wherein t=2–10; n is 1–10; and each (A-B) may be the same as or different from each other (A-B), where the somatostatin analog specifically binds to the somatostatin receptor; and (c) administering a neoplastic cell growth-arresting amount of the somatostatin analog to the animal. Preferably, the animal is a mammal (e.g., a human).

In a third aspect, the invention features a method for treating or alleviating a neoplasm in an animal that includes the steps of: (a) providing an animal including a somatostatin receptor-bearing neoplastic cell; (b) providing a detectably labeled somatostatin analog, where the detectable label is toxic and the analog has the formula:

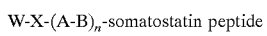
W-X-(A-B)$_n$-somatostatin peptide where A is D-tyrosine, L-tyrosine, D-3-iodotyrosine, L-3-iodotyrosine, D-3,5-diiodotyrosine, L-3,5-diiodotyrosine, D-4-aminophenylalanine, or L-4-aminophenylalanine; B is D-lysine, L-lysine, D-arginine, L-arginine, D- or L-1,3-diaminopropionic acid, D- or L-1,4-diaminobutanoic acid, D-NH$_2$—CH(Z)—CO$_2$H, or L-NH$_2$—CH(Z)—CO$_2$H, wherein Z is (CH$_2$)$_y$NH$_2$, wherein y is 1–10; X is A or B; W is absent or is NH$_2$(CH$_2$)$_t$CO, wherein t=2–10; n is 1–10; and each (A-B) may be the same as or different from each other (A-B), where the somatostatin analog specifically binds to the somatostatin receptor; and (c) administering a neoplastic cell growth-arresting amount of the somatostatin analog to the animal. Preferably, the animal is a mammal (e.g., a human).

In a fourth aspect, the invention features a method for imaging a somatostatin receptor-bearing cell in an animal that includes the steps of: (a) providing an animal including a somatostatin receptor-bearing cell; (b) providing a detectably labeled somatostatin analog of the formula:

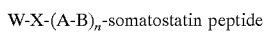
W-X-(A-B)$_n$-somatostatin peptide where A is D-tyrosine, L-tyrosine, D-3-iodotyrosine, L-3-iodotyrosine, D-3,5-diiodotyrosine, L-3,5-diiodotyrosine, D-4-aminophenylalanine, or L-4-aminophenylalanine; B is D-lysine, L-lysine, D-arginine, L-arginine, D- or L-1,3-diaminopropionic acid, D- or L-1,4-diaminobutanoic acid, D-NH$_2$—CH(Z)—CO$_2$H, or L-NH$_2$—CH(Z)—CO$_2$H, wherein Z is (CH$_2$)$_y$NH$_2$, wherein y is 1–10; X is A or B; W is absent or is NH$_2$(CH$_2$)$_t$CO, wherein t=2–10; n is 1–10; and each (A-B) may be the same as or different from each other (A-B), where the somatostatin analog specifically binds to the somatostatin receptor; and (c) administering the somatostatin analog to the animal, wherein the administration allows for the imaging of the cell. Preferably, the animal is a mammal (e.g., a human).

In a fifth aspect, the invention features a method for detecting, in an animal, a cell that expresses an abnormally high level of a somatostatin receptor that includes the steps of: (a) providing an animal including a cell that expresses an abnormally high level of a somatostatin receptor; (b) providing a detectably labeled somatostatin analog of the formula:

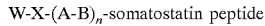

W-X-(A-B)$_n$-somatostatin peptide where A is D-tyrosine, L-tyrosine, D-3-iodotyrosine, L-3-iodotyrosine, D-3,5-diiodotyrosine, L-3,5-diiodotyrosine, D-4-aminophenylalanine, or L-4-aminophenylalanine; B is D-lysine, L-lysine, D-arginine, L-arginine, D- or L-1,3-diaminopropionic acid, D- or L-1,4-diaminobutanoic acid, D-NH$_2$—CH(Z)—CO$_2$H, or L-NH$_2$—CH(Z)—CO$_2$H, wherein Z is (CH$_2$)$_y$NH$_2$, wherein y is 1–10; X is A or B; W is absent or is NH$_2$(CH$_2$)$_t$CO, wherein t=2–10; n is 1–10; and each (A-B) may be the same as or different from each other (A-B), where the somatostatin analog specifically binds to the somatostatin receptor; and (c) administering the somatostatin analog to the animal, wherein the administration allows for the detection of the cell. Preferably, the animal is a mammal (e.g., a human).

In accordance with the present invention, by "somatostatin peptide" is meant a somatostatin analog having at least one biological activity of native somatostatin; preferably, this activity is the ability to specifically bind to a somatostatin receptor on a somatostatin receptor-bearing cell. Many such analogs having biological activity are known and have been described, for example, in Hornik et al., U.S. Pat. No. 5,770,687 (issued Jun. 23, 1998); Coy et al., U.S. Pat. No. 5,708,135 (issued Jan. 13, 1998); Hoeger et al., U.S. Pat. No. 5,750,499 (issued May 12, 1998); McBride et al., U.S. Pat. No. 5,620,675 (issued Apr. 15, 1997); Coy et al., U.S. Pat. No. 5,633,263 (issued May 27, 1997); Coy et al., U.S. Pat. No. 5,597,894 (issued Jan. 28, 1997); Taylor et al., U.S. Pat. No. 5,073,541 (issued Dec. 17, 1991); Coy et al., U.S. Pat. No. 4,904,642 (issued Feb. 27, 1990); and A. E. Bogden, U.S. Pat. No. 5,411,943 (issued May 2, 1995), each of which is hereby incorporated by reference.

By "specifically binds" is meant binding to a somatostatin receptor but not substantially to other molecules in a sample (e.g., a biological sample) that naturally includes protein. Preferably, a compound specifically binds to one type of a somatostatin receptor (e.g., somatostatin receptor type 4) but does not substantially bind to a second type of somatostatin receptor (e.g., somatostatin receptor type 5). Where a cell expresses a somatostatin receptor to which an analog of the invention specifically binds, that analog is capable of specifically targeting that cell. Preferably, the specifically targeted cell expresses a higher level of the specifically bound somatostatin receptor than other non-specifically targeted cells. For example, a neoplastic hepatic cell specifically targeted by an analog preferably expresses a higher level of the somatostatin receptor to which that analog specifically binds than a normal (i.e., non-neoplastic) hepatic cell.

By a "cell growth-arresting amount" is meant an amount of a compound (e.g., a somatostatin analog) which, when administered to a cell, results in the growth arrest of the administered cell. Such an amount may inhibit cell division, cause a reduction in the mass or volume of the administered cell, or induce death of the cell (e.g., by inducing apoptosis or by being directly cytotoxic).

By "detectable label" is meant any type of label which, when attached to an amino acid residue, renders that amino acid residue (and the peptide which contains that amino acid residue) detectable. A detectable label may be toxic or non-toxic, and may have one or more of the following attributes, without restriction: fluorescence, color, toxicity (e.g., radioactivity, e.g., a γ-emitting radionuclide, a β-emitting radionuclide, an α-emitting radionuclide, or a positron-emitting radionuclide), radiosensitivity, or photosensitivity. Although a detectable label may be directly attached to an amino acid residue of an analog of the invention, a detectable label may also be indirectly attached, for example, by being complexed with a chelating group that is attached (e.g., linked via a covalent bond or indirectly linked) to an amino acid residue of an analog. A detectably label may also be indirectly attached to an analog by the ability of the label to be specifically bound by a second molecule. One example of this type of an indirectly attached label is a biotin label that can be specifically bound by the second molecule, streptavidin. The second molecule may also be linked to a moiety that allows neutron capture (e.g., a boron cage as described in, for example, Kahl et al., Proc. Natl. Acad. Sci. USA 87:7265–7269, 1990).

A detectable label may also be a metal ion from heavy elements or rare earth ions, such as Gd$^{3+}$, Fe$^{3+}$, Mn$^{3+}$, or Cr$^{2+}$. Preferred radioactive detectable labels are short-acting radioactive iodine labels (e.g., $^{123}$I or $^{131}$I) that are capable of being coupled to each Tyr or 4-amino-Phe residue present in the analogs of the invention. Preferred non-radioactive detectable labels are the many known dyes that are capable of being coupled to NH$_2$-terminal amino acid residues.

By "toxic," in reference to a detectable label, is meant a detectable label which, when attached to an analog of the invention, confers to the detectably labeled analog an ability to adversely affect a cell bearing a receptor to which the detectably labeled analog specifically binds. Preferred examples of toxic detectable labels that may be indirectly or directly attached to the analogs described herein include ricin, diptheria toxin, and radioactive detectable labels (e.g., $^{131}$I, $^{123}$I, $^{125}$I, $^{111}$In, $^{195}$Pt, $^{193}$Pt, and $^{90}$Y). A toxic detectable label may also be a chemotherapeutic agent (e.g., 5-fluorouracil or adriamycin), or may be a radiosensitizing agent (e.g., Taxol, gemcitabine, fluoropyrimidine, metronitozil, or the deoxycytidine analog 2',2' difluoro-2'-deoxycytidine (dFdCyd)) to which is directly or indirectly attached a somatostatin analog of the present invention.

By "non-toxic," in reference to a detectable label, is meant a detectable label which, when attached to an analog of the invention, does not confer to the detectably labeled analog an ability to adversely affect a cell bearing a receptor to which the detectably labeled analog specifically binds.

By "pharmaceutically acceptable carrier" is meant a carrier that is physiologically acceptable to an administered animal while retaining the therapeutic properties of the compound with which it is administered. One exemplary pharmaceutically acceptable carrier is physiological saline. Other physiologically acceptable carriers and their formulations are known to one skilled in the art and described, for example, in *Remington's Pharmaceutical Sciences*, (18$^{th}$ edition), ed. A. Gennaro, 1990, Mack Publishing Company, Easton, Pa.

By "abnormally high level of expression" is meant a level of expression on a cell that is higher than the level of expression on a normal cell of that same cell type. For example, the level of expression of a somatostatin receptor subtype on a neoplastic pancreatic cell is compared to the level of expression of that same somatostatin receptor subtype on a normal (i.e., non-neoplastic) pancreatic cell. It will be understood that two neoplastic pancreatic cells in the same tumor may express different levels of a particular somatostatin receptor subtype; however, as long as the two neoplastic cells both express a higher level than a normal pancreatic cell, both have an abnormally high level of expression.

By "angiogenic blood vessel" is meant a blood vessel or a cell thereof (e.g., an endothelial cell) that is newly formed and expresses a higher level of a somatostatin receptor subtype than a non-angiogenic blood vessel. Preferably, an angiogenic blood vessel supplies a neoplastic cell mass.

The invention described herein provides novel reagents and methods for detecting and imaging somatostatin receptor-expressing cells, and for delivering cell death-conferring radioactivity to tumor cells expressing somatostatin receptors. The invention is based on our discovery that unlabeled and labeled (e.g., radiolabeled) somatostatin analogs can kill and/or cause cell growth arrest in somatostatin receptor bearing cells (e.g., neoplastic cells). Our findings are surprising given that recent publications have stated that because of their difficulty to obtain, radiolabeled somatostatin analogs are not feasible for somatostatin peptide receptor therapy (Bakker et al., Eur. J. of Nucl. Med. 23: 775–781, 1996; Breeman et al., Quarterly J. of Nucl. Med. 40: 209–220, 1996).

A somatostatin analog of the invention has a biological potency that is preferably greater than or equal to the parent somatostatin analog from which it is derived. Moreover, the analogs described herein bind to more somatostatin receptor subtypes than previous analogs. Some analogs of the invention contain D-Tyr, which may be iodinated, while retaining high receptor affinity and biological potency. Since D-iodotyrosine residues are protease resistant (Kawai et al., Nucl. Med. Biol 17: 369–376, 1990), these D-iodotyrosine-containing analogs do not rapidly undergo enzymatic deiodination and thus retain the iodine-attached amino acid residue-dependent detectable label (radioactive or non-radioactive).

Additionally, because the somatostatin analogs of the invention are hydrophilic, they are water-soluble and, thus, have enhanced use as compared to previous hydrophobic analogs. The hydrophilic analogs described herein are soluble in urine (and so are excreted by the kidney) as well as in blood, cerebral spinal fluid, and other bodily fluids. This hydrophilic character facilitates the delivery of the analogs of the invention to almost every area of the body.

Other features and advantages of the invention will be apparent from the following detailed description thereof, and from the claims.

DETAILED DESCRIPTION

A series of multi-tyrosine-containing analogs of the somatostatin peptide have been synthesized in which enhanced hydrophilicity and solubility has been introduced by the inclusion of additional basic "sandwiching" residues. These peptides have been tested for binding to somatostatin receptors and inhibition of release of growth hormone from rat pituitary cells (a type 2 receptor mediated event). Some analogs displayed enhanced biological potency, enhanced binding to type 2 receptors, and an enhanced affinity for type 1 and type 3 receptors and, thus, displayed a broader spectrum of biological activity than previous analogs.

Included among the somatostatin analogs synthesized thus far are the following:

D-Lys-Tyr-Lys-Tyr-Lys-c[Cys-Phe-D-Trp-Lys-Thr-Cys]-Thr-NH$_2$ (JF-05-59)
D-Arg-Tyr-Arg-Tyr-Arg-c[Cys-Phe-D-Trp-Lys-Thr-Cys]-Thr-NH$_2$ (JF-05-81)
D-Lys-Tyr-Lys-Tyr-Lys-Tyr-Lys-c[Cys-Phe-D-Trp-Lys-Thr-Cys]-Thr-NH$_2$ (JF-05-83)
D-Lys-Tyr-Lys-D-Tyr-D-Lys-Tyr-Lys-c[Cys-Phe-D-Trp-Lys-Thr-Cys]-Thr-NH$_2$ (JF-05-85)
Dap-Tyr-Dap-Tyr-Dap-c[Cys-Phe-D-Trp-Lys-Thr-Cys]-Thr-NH$_2$ (JF-05-43) (Dap=1,3 diaminopropionic acid)
D-Lys-D-Tyr-D-Lys-D-Tyr-D-Lys-c[Cys-Phe-D-Trp-Lys-Thr-Cys]-Thr-NH$_2$ (JF-05-44)
D-Lys-Pap-Lys-Pap-Lys-c[Cys-Phe-D-Trp-Lys-Thr-Cys]-Thr-NH$_2$ (JF-06-31) (Pap=4-aminophenylalanine, which can be iodinated)
Dab-Tyr-Dab-Tyr-Dab-c[Cys-Phe-D-Trp-Lys-Thr-Cys]-Thr-NH$_2$ (JF-06-45) (Dab=1,4-diaminobutanoic acid)
D-Lys-D-Tyr-D-Lys-c[Cys-Phe-D-Trp-Lys-Thr-Cys]-Thr-NH$_2$ (JF-06-50)
D-Lys-D-Tyr-Lys-D-Tyr-D-Lys-c[Cys-Phe-D-Trp-Lys-Thr-Cys]-Thr-NH$^2$ (JF-06-57)

The analogs of the invention may be labeled by a variety of methods described herein, or may be used unlabeled. A preferable method for labeling the analogs of the invention is to directly attach one of the many short-acting radioactive or non-radioactive iodine labels to each Tyr or 4-amino-Phe residue. In addition, by attaching a chelating group (e.g., an iminodicarboxylic group or a polyaminopolycarboxylic group) to an analog of the invention using the methods generally described in Albert et al., U.S. Pat. No. 5,753,627 (issued May 19, 1998) and PCT Publication No. WO 91/01144 (published Feb. 7, 1991) (both of which are hereby incorporated by reference), an analog of the invention may be complexed, through its attached chelating agent, to a detectable label (e.g., a photosensitizing agent), thereby resulting in an analog that is indirectly labeled.

Attachment of detectable labels to the analogs of the invention results in highly detectable somatostatin receptor ligands which specifically bind to somatostatin receptors present in large numbers on many types of cells, including human tumor cells. Thus, the analogs described herein provide reagents and improved methods for the imaging of somatostatin receptor-bearing cells (e.g., the tumors). It will be understood that the type of label, if any, will depend upon the type of cell targeted, the level of targeted receptor expression on the surrounding cells, and the homogeneity (or lack thereof) of expression on the targeted cell population.

Preferably, a somatostatin analog which specifically binds a particular subtype of somatostatin receptor and bearing a radioactive iodine label may be used to deliver high doses of cell-death conferring radioactivity to tumor cells expressing high levels of that somatostatin receptor subtype (e.g., somatostatin receptor type 2). Thus, where a certain type of tumors express a particular type of somatostatin receptor, an analog that particularly targets that receptor type (i.e., has a higher affinity for receptor type 2 than receptor types 1, 3, 4, and 5) may be employed.

An advantage that the multiple Tyr-containing peptide analogs of the present invention have over previous approaches is that the analogs of the invention have been found to retain or exceed the biological potencies of their parent somatostatin analogs. In addition, the analogs described herein bind to more receptor subtypes than previously described analogs. Furthermore, the analogs described herein which contain D-Tyr retain high receptor affinity and biological potency. Since these D-iodo-Tyr derivatives do not undergo enzymatic deiodination as do their L-counterparts, the D-iodo-Tyr containing analogs of the invention retain their label for longer than analogs not containing at least one such residue.

Moreover, previous somatostatin analogs were very lipophilic (i.e., hydrophobic), which allowed the compounds to become concentrated in the liver. This created problems because, where a labeled analog was used for tumor imaging and intraoperative localization, the entire liver became labeled, making the tumors in the liver difficult to detect over the background normal liver. An advantage of the somatostatin analogs described herein is their hydrophilicity. Hydrophilic compounds are water-soluble and, thus, are excreted by the kidney into the urine. Hence, if there is a tumor in the liver, use of a hydrophilic analog of the invention will allow the visualization of the tumor over the background unlabeled healthy liver.

In vitro Effects on Rat Pituitary Growth Hormone (GH) Release

The rat pituitary growth hormone release assay used to test the biological potency of the somatostatin analogs of the invention is a primary system for evaluating SRIF analog potency and is a somatostatin subtype 2 rat receptor related system.

Anterior pituitaries from adult male rats weighing 200–250 grams and housed under controlled conditions (lights on from 0500–1900 hours), were dispersed using aseptic techniques by a trypsin/DNase method (see, e.g., the method described in Chang et al., Gen. Comp. Endocrinol. 77: 256–273, 1990). The dispersed cells were diluted with sterile-filtered Dulbecco's modified Eagle medium (MEM) (GIBCO Laboratories, Grand Island, N.Y.) supplemented with 2.5% fetal calf serum (GIBCO), 3% horse serum (GIBCO), 10% fresh rat serum (stored on ice for no longer than 1 hour) from the pituitary donors, 1% MEM nonessential amino acids (GIBCO), gentamycin (10 ng/ml; Sigma Chemical Co., St. Louis, Mo.) and nystatin (10,000 U/ml; GIBCO). The cells were counted with a hemacytometer (approximately 2,000,000 cells per pituitary) and randomly plated at a density of 200,000 cells per well (Co-Star cluster 24;Rochester Scientific Co., Rochester, N.Y.). The plated cells were maintained in the above-described Dulbecco's medium in a humidified atmosphere of 95% air and 5% $CO_2$ at 37° C. for 96 hours.

In preparation for a hormone challenge, the cells were washed 3x with medium 199 (GIBCO) to remove old medium and floating cells. Each dose of secretagogue GRH (1-29) (diluted in siliconized test tubes; commercially available from, e.g., Bachem Bioscience Inc., King of Prussia, Pa.) was tested in quadruplicated wells in a total volume of 1 ml medium 199 containing 1% BSA (fraction V; Sigma). Cells were pulsed with doses of somatostatin or somatostatin analogs in the presence of GH-stimulatory 1 nM GRH(1-29) $NH_2$. After 3 hours at 37° C. in an air/carbon dioxide (95/5%) atmosphere, the medium was removed and stored at 20° C. until assayed for hormone content. GH in plasma and media was measured by a standard double antibody radioimmunoassay (RIA) using components supplied by the National Institute of Diabetes and Digestive and Kidney Diseases and the National Hormone and Pituitary Program (contact Dr. A. F. Parlow, Scientific Director, Harbor-UCLA Medical Center, 1000 West Carson St., Torrance, Calif. 90509). Using this rat pituitary cell system, the inhibitory potency, represented as $IC_{50}$ (nM), for the indicated somatostatin analogs of the invention is shown on Table I.

TABLE I

Biological activities of selected analogs

| Compound | $IC_{50}$ (nM)[a] | $K_d$ (nM) for human SRIF receptors | | | | |
|---|---|---|---|---|---|---|
| | | type 1 | type 2 | type 3 | type 4 | type 5 |
| JF-05-59 | 0.3 | 4.1 | 0.36 | 6.4 | 515 | 13.4 |
| JF-05-59(I)* | 0.26 | nd | nd | nd | nd | nd |
| JF-05-81 | nd | 12.1 | 0.28 | 14.6 | >1000 | 3.3 |
| JF-05-85 | 0.86 | 16.9 | 0.38 | 15.1 | 369 | 17.3 |
| JF-06-31 | 0.18 | 1.5 | 0.09 | 20.8 | >1000 | 3.0 |
| JF-06-43 | 1.44 | 7.5 | 2.4 | 84.9 | >1000 | 8.9 |
| JF-06-44 | 2.1 | 3.8 | 0.87 | 0.91 | nd | 17.0 |
| JF-06-45 | 7.1 | 6.2 | 1.37 | 22.7 | >1000 | 115 |
| JF-06-50 | 2.79 | 20.9 | 1.96 | 4.87 | >1000 | 20.0 |
| SRIF | — | 2.0 | 0.25 | 1.2 | 1.8 | 1.4 |
| octreotide[b] | — | >1000 | 0.57 | 28.8 | >1000 | 6.8 |

[a]Inhibitory potency using rat pituitary cell system
*This is fully iodinated JF-05-59 (iodinated on both tyrosine residues) in which is preserved high potency (i.e., an equivalent $IC_{50}$ in both non-iodinated ($IC_{50}$ = 0.3 nM) and iodinated ($IC_{50}$ = 0.26 nM)).
[b]Used as a control for comparison; also called Sandostatin.
nd, not done

Radioligand Binding Assays

Also shown in Table I are the affinity constants, represented as $K_d$, for human SRIF receptors types 1–5 of the indicated somatostatin analogs of the invention.

For this study, cell membranes were obtained from homogenates of CHO-K1 cells (Chinese hamster ovary cells) ectopically expressing one of the five known somatostatin receptor subtypes (the cells were transfected with cDNA encoding a somatostatin receptor subtype, according to standard methods (see, e.g., Ausubel et al., *Current Protocols in Molecular Biology*, John Wiley & Sons, New York, N.Y., 1994)). Aliquots of the membranes were incubated (30 min, at 37° C.) with 0.05 nM $^{125}$I-Tyr11-SRIF (which specifically binds somatostatin receptor types 1,3,4,5) or $^{125}$I-MK-678 (an analog that specifically binds somatostatin receptor type 2) in 50 nM HEPES (pH 7.4) containing BSA (10 mg/ml), $MgCl_2$ (5 mM), Trasylol (200 KIU/ml), bacitracin (0.02 mg/ml), and phenylmethylsulphonyl fluoride (0.02 mg/ml). The final assay volume was 0.3 ml. Incubations were terminated by rapid filtration through GF/C filters pre-soaked in 0.3% polyethylenimine using a 2 Brandel rapid filtration module (48 wells each). Each tube and filter was then washed 3 times with 5 ml aliquots of cold buffer. Specific binding was defined as the total radioligand bound minus that bound in the presence of 1000 nM SRIF analog, which was not labeled. Hence, the "cold" analog of the invention competed off the "hot" $^{125}$I-Tyr11-SRIF or $^{125}$I-MK-678 analog, thus allowing the binding affinity to be determined.

Labeling

The somatostatin analogs of the invention may be used unlabeled to specifically target somatostatin receptor bearing cells (e.g., tumor cells) and, for example, arrest the growth of these cells. The analogs may also be detectably labeled with either a toxic or non-toxic label that is either directly or indirectly attached to an amino acid residue of the analog. Furthermore, a labeled somatostatin analog may bear more than one label. For example, the same molecule (e.g., JF-05-44) may be directly labeled with radioactive iodine on an internal D-Tyr residue and indirectly labeled with a non-toxic label (e.g., fluoroscein) attached to the N-terminal L-Lys residue via a chelating group. This dual labeling is particularly useful where a low-emitting radiolabel (e.g., an auger electron emitter) is used (see below). Likewise, the same molecule (e.g., JF-06-57) may be dually labeled with two different isotopes. For example, the D-Tyr residues may be radiolabeled by being iodinated with $^{123}$I, while the molecule may be additionally radiolabeled with, for example, $^{90}$Y, which may be indirectly attached via a bifunctional stable chelator to the side arm of an internal amino acid residue, and/or may be attached to either (or both) of the N- or C-termini. By being dual labeled, where the other label is, for example, a visually-detectable dye, an analog is easily traced while not being overly toxic. Such a low-toxicity dually labeled analog may be useful in the treatment of widely dispersed small neoplastic cell masses (e.g., metastatic breast cancer cells that have metastasized to various lymph nodes of the body).

Radioactive detectable labels are preferred toxic labels for the specific targeting of neoplastic cells; however, it should be noted that the type of radioactive label will depend upon the type of tumor being treated. For example, a tumor consisting of cells each expressing the same number of a somatostatin receptor subtype (e.g., type 2) may be targeted by administering a somatostatin analog of the invention labeled with a low energy emitter (e.g., auger electron emitters $^{125}$I or $^{111}$In). Where the cells in a targeted tumor are not homogeneous in their expression of a somatostatin receptor subtype (e.g., one neoplastic cell expresses 100,000 somatostatin receptor type 2 molecules while an adjacent neoplastic cell expresses only 10,000 somatostatin receptor type 2 molecules), a somatostatin analog labeled with a higher energy emitter (e.g., $^{90}$Y) may be used.

Auger electron emitter-labelled analogs may also be used where the tumor cells, but not the surrounding normal cell, express a particular somatostatin receptor, since auger electron emitters, although not very lethal extracellularly, are very lethal when internalized. Thus, a tumor cell expressing a somatostatin receptor will bind and internalize the auger electron emitter-labeled analog, and thus be destroyed. Where internalization is desired, it is important to construct the analog to contain at least some D-isomers of amino acids (e.g., an analog containing D-Tyr) instead of an analog containing only L-isomer amino acids, since L-isomer amino acid analogs tend to bind early and are rapidly degraded while D-isomer amino acid analogs (or analogs having a mixture of D-isomers and L-isomers) do not degrade as quickly and, as a result, are internalized when they bind. In addition, as mentioned above, analogs containing D-Tyr are also protease insensitive.

It should be noted that radiolabeled analogs of the invention (e.g., iodinated or halogenated) may be used with standard imaging techniques, such as positron-emission topography, to visualize the location of a tumor. One preferred method of the invention is the intraoperative (e.g., for tumor localization and detection) use of radiolabelled somatostatin analogs to detect small deposits of tumor cells. Where the radiolabel is a γ-ray emitter, the tumors can be localized with a standard hand-held Geiger counter (i.e., a γ-ray detector).

Analogs of the invention may also be labeled with agents that render them (and the cells to which they are bound) abnormally sensitive to radioactivity or light. For example, a radiosensitizer, such as deoxycytidine analog 2',2'difluoro-2'-deoxycytidine (dFdCyd; Lawrence et al., Int. J. Radiat. Oncol. Biol. Phys. 34:867–872, 1996), may be indirectly or directly attached to an analog of the invention. Following administration of such a radiosensitizer labeled analog, a cancer patient is exposed to a non-lethal amount of radioactivity, thus arresting the growth of the tumor. Likewise, an analog of the invention may be directly or indirectly labeled with a photosensitizer (i.e., light absorbing compound; reviewed in Pandey and Herman, Chemistry and Industry, Sep. 21, 1998 issue, pages 739–743, 1998). In this method, the photosensitizer labeled analog is allowed to accumulate within the cell before being activated with light. Thus, the preferred analog to be labeled with a photosensitizer should comprise at least one D-isomer amino acid residue (preferably D-Tyr) to prevent rapid degradation of the analog.

Use

When administered to an animal (e.g., a human), a somatostatin analog of the invention may be used to inhibit growth hormone release and/or therapeutically affect the central nervous system. When labeled, a somatostatin analog may be used, for example, for the imaging or detection of a somatostatin receptor bearing cell. Preferably, the employed analog has a high affinity for the type of somatostatin receptor expressed on the targeted cell. For example, if the cells desired to be imaged are human brain cells, the labeled analog employed preferably binds with higher affinity to the human somatostatin receptor types 1, 2, and 4 than the other somatostatin receptor types.

A radiolabeled somatostatin analog (or an analog labeled with another toxin, such as ricin) may also be employed to selectively kill or arrest the growth of a neoplastic cell expressing a somatostatin receptor. Again, the analog selected for use preferably specifically binds to the particular type of somatostatin receptor expressed on the targeted neoplastic cell, as opposed to binding to other types of somatostatin receptors. For example, for human neuroblastoma, an analog that specifically binds to the human somatostatin receptor type 2 is preferably employed.

Most preferably, prior to treatment, a portion of the tumor is removed by biopsy and examined for the level of expression of the different types of somatostatin receptor. If the tumor to be specifically targeted expresses a higher level of somatostatin receptor type 5 than other types of somatostatin receptor and/or if there is a reduced level of expression of somatostatin receptor type 5 on the surrounding normal tissue, an analog with high affinity to somatostatin type 5 should be employed for imaging and treatment.

Another use for a somatostatin analog of the invention is the specific targeting of angiogenic blood vessels supplying cells (e.g., neoplastic cells). For example, angiogenic blood vessels express somatostatin receptor type 2, while normal blood vessels do not. Thus, a somatostatin analog, which may be labeled with a toxin (e.g., radiolabeled or indirectly labeled to a chemotherapeutic agent, such as 5-fluorouracil) may be used to selectively target and arrest the growth of angiogenic blood vessels. Given the hydrophilicity of the somatostatin analogs described herein, the analogs may be administered directly into the blood. Since the hydrophilicity of the analogs allows them to be soluble in water-based liquid (such as blood), the analogs will be carried past the normal blood vessel cells not expressing somatostatin receptor type 2 to the angiogenic blood vessel cells. Of course, preferably, the analog used for specifically targeting angiogenic blood vessel cells will have a high affinity for somatostatin receptor type 2.

While a preferred use for a somatostatin analog that targets angiogenic blood vessel cells is the specific targeting of blood vessel cells supplying nutrients to tumor cells, it will be understood that the analog may be used to specifically target any angiogenic blood vessel cells. Thus, the analogs described herein may be used to target angiogenic blood vessel cells involved in human diseases including, without limitation, psoriasis, protective retinopathy, and diabetes-related blindness.

Administration

A somatostatin analog of the invention may be administered within a pharmaceutically-acceptable diluent, carrier, or excipient, in unit dosage form. Conventional pharmaceutical practice may be employed to provide suitable formulations or compositions to administer somatostatin analogs to patients for imaging or anti-neoplastic treatment. Administration may begin before the patient is symptomatic (i.e., adjuvant therapy) or before the patient has had any detectable tumor using conventional methods (e.g., palpation). Any appropriate route of administration may be employed, for example, administration may be by direct injection into the tumor, direct injection in a blood vessel supplying nutrients to the tumor, as well as parenteral, intravenous, intra-arterial, intra-vitreal, intra-vesicular (i.e., into the bladder), subcutaneous, intramuscular, intracranial, intraorbital, ophthalmic, intraventricular, intracapsular, intraspinal, intrathecal, intracistemal, intraperitoneal, intranasal, aerosol, by suppositories, or oral administration. Therapeutic formulations may be in the form of liquid solutions, suspensions, or semi-solid or solid gels; for oral administration, formulations may be in the form of tablets or capsules; and for inhalational or intranasal formulations, in the form of powders, nasal drops, or aerosols. In addition, an analog of the invention may be administered with collagen gelfoam (i.e., an arteriole embolic agent), or may be administered such that sustained release of the analog is achieved (e.g., by administration with an oily composition such as Lipidiol).

Methods well known in the art for making formulations are found, for example, in *Remington's Pharmaceutical Sciences* (18$^{th}$ edition), ed. A. Gennaro, 1990, Mack Publishing Company, Easton, Pa. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. Other potentially useful parenteral delivery systems for somatostatin analogs include ethylene-vinyl acetate copolymer particles, osmotic pumps, implantable infusion systems, and liposomes. Formulations for inhalation may contain excipients, for example, lactose, or may be aqueous solutions containing, for example, polyoxyethylene-9-lauryl ether, glycocholate and deoxycholate, or may be oily solutions for administration in the form of nasal drops, or as a gel.

If desired, anti-neoplastic treatment with a radiolabeled somatostatin analog may be combined with more traditional therapies for the disease such as surgery, steroid therapy, radiotherapy, or chemotherapy.

In the following examples, we describe the synthesis of some of the somatostatin analogs of the invention. These examples are meant to illustrate the invention, and do not limit the invention in any way.

EXAMPLE I

Boc-N,2-chlorobenzyloxycarbonyl-D-lysine-O-dichlorobenzyl-tyrosine-N,2-chlorobenzyloxycarbonyl-lysine-O-dichlorobenzyl-tyrosine-N,2-chlorobenzyloxycarbonyl-lysine-S,4-methylbenzyl-cysteine-phenylalanine-D-tryptophan-N,2-chlorobenzyloxycarbonyl-lysine-O-benzyl-threonine-S,4-methylbenzyl-cysteine-O-benzyl-threonine-benzhydrylamine resin 4-Methyl-benzhydrylamine polystyrene resin (Bachem Bioscience Inc., King of Prussia, Pa.) (1.09 g, 0.25 mmole) in the chloride ion form was placed in the reaction vessel of a CS Bio peptide synthesizer programmed to perform the following reaction cycle: (a) methylene chloride; (b) 40% trifluoroacetic acid in methylene chloride (2 times for 2 and 20 minutes each); (c) methylene chloride; (d) methylene chloride; and (e) 10% diisopropylethylamine in N,N-dimethylformamide (2 times for 2 and 5 minutes each).

The neutralized resin was mixed with Boc-O-benzyl-threonine and diisopropylcarbodiimide (1.0 mmole each) in methylene chloride for 1 hour. The resulting amino acid resin was then cycled through steps (a) to (e) in the above-described wash program. The following amino acids (1.0 mmole each) were then coupled successively by the same procedure: Boc-S,4-methylbenzyl-cysteine, Boc-O-benzyl-threonine, Boc-N,2-chlorobenzyloxycarbonyl-lysine, Boc-D-tryptophan, Boc-phenylalanine, Boc-S,4-methylbenzyl-cysteine, Boc-N,2-chlorobenzyloxycarbonyl-lysine, Boc-O-dichlorobenzyl-tyrosine, Boc-N,2-chlorobenzyloxycarbonyl-lysine, Boc-O-dichlorobenzyl-tyrosine, and Boc-N,2-chlorobenzyloxycarbonyl-D-lysine.

EXAMPLE II

D-Lysine-tyrosine-lysine-tyrosine-lysine-cyclic (cysteine-phenylalanine-D-tryptophan-lysine-threonine-cysteine)-threonine-NH$_2$ (JF-05-59)

The peptide bound resin described in Example I was mixed with anisole (5 ml), and anhydrous hydrogen fluoride (35 ml) at 0° C., and stirred for 45 min. Excess hydrogen fluoride was evaporated rapidly under a stream of dry nitrogen and free peptide precipitated and washed with ether. The crude peptide was then dissolved in 500 ml of 90% acetic acid to which a concentrated solution of I$_2$/MeOH was added until a permanent brown color was observed. Excess I$_2$ was removed by addition of ascorbic acid and the solution evaporated to a small volume which was applied to a strong cation exchange column. The peptide was eluted with a linear gradient of 0.5 M NaCl in 0.1% trifluoroacetic acid in 30% acetonitrile. Fractions of correct molecular weight were pooled and evaporated to a small volume, and were then further purified by applying to a column (4×20 cm) of Rainin octadecylsilane silica (8 μm). The peptide was eluted with a linear gradient of acetonitrile in 0.1% trifluoroacetic acid in water. Fractions were examined by analytical high performance liquid chromatography and pooled to give maximum purity. Lyophilization of the solution from water gave the desired product as a white, fluffy powder.

The final product was found to be homogeneous by HPLC and MALDI-TOF mass spectrometry. Amino acid analysis of an acid hydrolysate and MALDI-TOF MS confirmed the composition of the peptide.

EXAMPLE III

Boc-N,2-chlorobenzyloxycarbonyl-D-lysine-O-dichlorobenzyl-D-tyrosine-N,2-chlorobenzyloxycarbonyl-D-lysine-O-dichlorobenzyl-D-tyrosine-N,2-chlorobenzyloxycarbonyl-D-lysine-S,4-methylbenzyl-cysteine-phenylalanine-D-tryptophan-N,2-chlorobenzyloxycarbonyl-lysine-O-benzyl-threonine-S,4-methylbenzyl-cysteine-O-benzyl-threonine-benzhydrylamine resin 4-Methyl-benzhydrylamine polystyrene resin (Bachem Bioscience Inc., King of Prussia, Pa.) (1.09 grams, 0.25 mmole) in the chloride ion form was placed in the reaction vessel of a CS Bio peptide synthesizer programmed to perform the following reaction cycle: (a) methylene chloride; (b) 40% trifluoroacetic acid in methylene chloride (2 times for 2 and 20 minutes each); (c) methylene chloride; (d) methylene chloride; and (e) 10% diisopropylethylamine in N,N-dimethylformamide (2 times for 2 and 5 minutes each).

The neutralized resin was mixed with Boc-O-benzyl-threonine and diisopropylcarbodiimide (1.0 mmole each) in methylene chloride for 1 hour and the resulting amino acid resin was then cycled through steps (a) to (e) in the above-described wash program. The following amino acids (1.0 mmole) were then coupled successively by the same procedure: Boc-S,4-methylbenzyl-cysteine, Boc-O-benzyl-threonine, Boc-N,2-chlorobenzyloxycarbonyl-lysine, Boc-D-tryptophan, Boc-phenylalanine, Boc-S,4-methylbenzyl-cysteine, Boc-N,2-chlorobenzyloxycarbonyl-D-lysine, Boc-O-dichlorobenzyl-D-tyrosine, Boc-N,2-chlorobenzyloxycarbonyl-D-lysine, Boc-O-dichlorobenzyl-D-tyrosine, and Boc-N,2-chlorobenzyloxycarbonyl-D-lysine.

EXAMPLE IV

D-Lysine-D-tyrosine-D-lysine-D-tyrosine-D-lysine-cyclic(cysteine-phenylalanine-D-tryptophan-lysine-threonine-cysteine)-threonine-$NH_2$ (JF-05-44)

The peptide bound resin described in Example III was mixed with anisole (5 ml), and anhydrous hydrogen fluoride (35 ml) at 0° C. and stirred for 45 min. Excess hydrogen fluoride was evaporated rapidly under a stream of dry nitrogen and free peptide precipitated and washed with ether. The crude peptide was then dissolved in 500 ml of 90% acetic acid to which a concentrated solution of $I_2$/MeOH was added until a permanent brown color was observed. Excess $I^2$ was removed by addition of ascorbic acid and the solution evaporated to a small volume which was applied to a strong cation exchange column. The peptide was eluted with a linear gradient of 0.5 M NaCl in 0.1% trifluoroacetic acid in 30% acetonitrile. Fractions of correct molecular weight were pooled and evaporated to a small volume, and were then further purified by applying to a column (4×20 cm) of Rainin octadecylsilane silica (8 μm). The peptide was eluted with a linear gradient of acetonitrile in 0.1% trifluoroacetic acid in water. Fractions were examined by analytical high performance liquid chromatography and pooled to give maximum purity. Lyophilization of the solution from water gave the desired product as a white, fluffy powder.

The final product was found to be homogeneous by HPLC and MALDI-TOF mass spectrometry. Amino acid analysis of an acid hydrolysate and MALDI-TOF MS confirmed the composition of the peptide.

EXAMPLE V

D-Lysine-D-diiodotyrosine-D-lysine-D-diiodotyrosine-D-lysine-cyclic(cysteine-phenylalanine-D-tryptophan-lysine-threonine-cysteine)-threonine-$NH_2$ (JIC-2D) was Made as Follows A specific amount of purified lyophilized peptide from Example IV was weighed out and dissolved in deionized water. Equivalent molar amounts were determined for sodium iodide, chloramine-T and sodium metabisulfite. 0.5 M phosphate buffer was added to the sodium iodide, chloramine-T, and sodium metabisulfite. Appropriate volumes of the sodium iodide, chloramine-T were added to the peptide and the oxidation reaction was allowed to proceed for 20 seconds. After 20 seconds, excess sodium metabisufite was added to stop the reaction. The reaction mixture was then applied to a C18 Seppak cartridge (Waters Corp., Milford, Mass.), washed with 10 mls of deionized water, washed with 16% acetonitrile in 0.1% trifluroracetic acid, and the peptide was eluted with 80% acetonitrile in 0.1% trifluoroacetic acid. Lyophilization of the solution from water gave the desired product as a white, fluffy powder.

The final product was found to be homogeneous by HPLC and MALDI-TOF mass spectrometry. MALDI-TOF MS confirmed the composition of the peptide.

OTHER EMBODIMENTS

Although the above examples describe chemical synthesis of the somatostatin analogs of the invention, it will be understood that any of these peptides may be generated according to standard molecular biology techniques. For example, cloned nucleic acids encoding a somatostatin analog may be obtained as described by L. M. Sabatini et al. (Biochem. Biophys. Res. Comm. 160: 495–502, 1989) and J. C. Vanderspek et al. (Arch. Oral Biol. 35: 137–43, 1990). cDNA encoding the somatostatin analog peptides can be cloned by recombinant DNA techniques, for instance, by using degenerate oligonucleotides based on the amino acid sequence of a somatostatin analog as primers for polymerase chain reaction amplification.

Alternatively, oligonucleotides encoding somatostatin analogs can be synthesized chemically using commercially available equipment. They can then be made double-stranded (e.g., using DNA polymerase I) and cloned into vectors for amplification. The somatostatin analogs can be produced in a variety of expression vector/host systems, which are available commercially (e.g., from the American Type Culture Collection, Manassas, Va.) or can be reproduced according to recombinant DNA and cell culture techniques. The vector/host expression systems can be prokaryotic or eukaryotic, and can include bacterial, yeast, insect, mammalian, and viral expression systems (such as are commercially available from, for example, Clontech Laboratories Inc., Palo Alto, Calif.). The construction of expression vectors encoding somatostatin analogs, transfer of the vectors into various host cells, and production of peptides from transformed host cells can be accomplished using genetic engineering techniques, as described in manuals such as Pouwels et al., *Cloning Vectors: A Laboratory Manual*, 1985, Supp. 1987;Ausubel et al., supra; and Sambrook et al., *Molecular Cloning: A Laboratory Manual*, Second Edition, Cold Spring Harbor Laboratory Press, 1989.

The somatostatin analog peptides encoded by expression vectors may be modified by post-translational processing in a particular expression vector/host cell system. In addition, these analogs can be altered by minor chemical modifications, such as by adding small substituents or by modifying one or more of the covalent bonds within or between the amino acid residues. The substituent groups can be bulky and may include one or more natural or modified amino acids. Useful modifications include the addition of a substituent to either the amino terminus, the carboxyl terminus, or to both termini of the peptide. Particularly useful modifications include acylation or carbamylation of the amino terminus of the peptide, or amidation of the carboxyl terminus of the peptide.

All publications and patent applications mentioned in this specification are herein incorporated by reference to the same extent as if each independent publication or patent application was specifically and individually indicated to be incorporated by reference.

While the invention has been described in connection with specific embodiments thereof, it will be understood that it is capable of further modifications and this application is intended to cover any variations, uses, or adaptations of the invention following, in general, the principles of the invention and including such departures from the present disclosure that come within known or customary practice within the art to which the invention pertains and may be applied to the essential features hereinbefore set forth, and follows in the scope of the appended claims.

Other embodiments are within the claims.

What is claimed is:

1. A compound comprising a somatostatin analog of the formula:

W-X-(A-B)$_n$-somatostatin peptide wherein:
  A is D-tyrosine, L-tyrosine, D-3-iodotyrosine, L-3-iodotyrosine, D-3,5-diiodotyrosine, L-3,5-diiodotyrosine, D-4-aminophenylalanine, or L-4-aminophenylalanine;
  B is D-lysine, L-lysine, D-arginine, L-arginine, D- or L-1,3-diaminopropionic acid, D- or L-1,4-diaminobutanoic acid, D-NH$_2$—CH(Z)—CO$_2$H, or L-NH$_2$—CH(Z)—CO$_2$H, wherein Z is (CH$_2$)$_y$NH$_2$, wherein y is 1–10;
  X is A or B;
  W is NH$_2$(CH$_2$)$_t$CO, wherein t=2–10, or is absent;
  n is 1–10; and each (A-B) may be the same as or different from each other (A-B).

2. The analog of claim 1, wherein said analog is attached to a detectable label.

3. The analog of claim 2, wherein said detectable label is toxic.

4. The analog of claim 2, wherein said detectable label is non-toxic.

5. The analog of claim 2, wherein said analog is indirectly attached to said detectable label.

6. The analog of claim 5, wherein said analog is attached to a chelating group that is attached to said detectable label.

7. The analog of claim 2, wherein said analog is directly attached to said detectable label.

8. The analog of claim 2, wherein said detectable label is an iodine label that is attached to a tyrosine residue or a phenylalanine residue of said analog.

9. The analog of claim 3, wherein said toxic detectable label is radioactive.

10. The analog of claim 8, wherein said analog comprises a tyrosine residue.

11. The analog of claim 10, wherein said iodotyrosine residue of said analog does not undergo enzymatic deiodination.

12. The analog of claim 1, wherein said analog has a biological activity that is greater than or equal to the biological activity of the somatostatin peptide of said analog.

13. A method of selectively targeting and arresting the growth of an angiogenic blood vessel or a cell thereof in a subject, said method comprising administering a somatostatin analog of claim 1 to said subject.

14. Pharmaceutical composition comprising compound of claim 1 and a pharmaceutically acceptable carrier.

15. A method for treating or alleviating a neoplasm in an animal, said method comprising the steps of:
  (a) providing an animal comprising a somatostatin receptor-bearing neoplastic cell;
  (b) providing a somatostatin analog of claim 1, wherein said somatostatin analog specifically binds to said somatostatin receptor; and
  (c) administering a neoplastic cell growth-arresting amount of said somatostatin analog to said animal.

16. A method for treating or alleviating a neoplasm in an animal, said method comprising the steps of:
  (a) providing an animal comprising a somatostatin receptor-bearing neoplastic cell;
  (b) providing a somatostatin analog of claim 3, wherein said somatostatin analog specifically binds to said somatostatin receptor; and (c) administering a neoplastic cell growth-arresting amount of said somatostatin analog to said animal.

17. A method for imaging a somatostatin receptor-bearing cell in an animal, said method comprising the steps of:
   (a) providing an animal comprising a somatostatin receptor-bearing cell;
   (b) providing a somatostatin analog of claim 2, wherein said somatostatin analog specifically binds to said somatostatin receptor; and
   (c) administering said somatostatin analog to said animal, wherein said administration allows for the imaging of said cell.

18. A method for detecting, in an animal, a cell that expresses an abnormally high level of a somatostatin receptor, said method comprising the steps of:
   (a) providing an animal comprising a cell expressing an abnormally high level of a somatostatin receptor;
   (b) providing a somatostatin analog of claim 2, wherein said somatostatin analog specifically binds to said somatostatin receptor; and
   (c) administering said somatostatin analog to said animal, wherein said administration allows for the detection of said cell.

19. The method of claim 15, 16, 17, or 18, wherein said animal is a human.

20. The method of claim 13, 15, 16, 17, 18, wherein said analog is administered with a pharmaceutically-acceptable carrier.

* * * * *

```
                         SEQUENCE LISTING

<160> NUMBER OF SEQ ID NOS: 1

<210> SEQ ID NO 1
<211> LENGTH: 14
<212> TYPE: PRT
<213> ORGANISM: Homo sapiens
<220> FEATURE:
<221> NAME/KEY: MOD_RES
<222> LOCATION: 3,14
<223> OTHER INFORMATION: Cys at positions 3 and 14 are circularized

<400> SEQUENCE: 1

Ala Gly Cys Lys Asn Phe Phe Trp Lys Thr Phe Thr Ser Cys
1               5                   10
```